(12) United States Patent
Ylänen et al.

(10) Patent No.: US 6,248,344 B1
(45) Date of Patent: Jun. 19, 2001

(54) COMPOSITE AND ITS USE

(76) Inventors: Heimo Ylänen, Skepparegatan 2 A 30; Hannu Aro, Valtaojantie 4, both of Fin-20810, Turku; Kaj Karlsson, Dragonvägen 48, Fin-20720, Åbo; Antti Yli-Urpo, Värttinäkatu 17, Fin-20660, Littoinen, all of (FI)

(*) Notice: Subject to any disclaimer, the term of this patent is extended or adjusted under 35 U.S.C. 154(b) by 0 days.

(21) Appl. No.: 09/381,229
(22) PCT Filed: Apr. 15, 1998
(86) PCT No.: PCT/FI98/00331
  § 371 Date: Sep. 17, 1999
  § 102(e) Date: Sep. 17, 1999
(87) PCT Pub. No.: WO98/47465
  PCT Pub. Date: Oct. 29, 1998

(30) Foreign Application Priority Data

Apr. 21, 1997 (FI) .................... 971692

(51) Int. Cl.⁷ .......... A61F 2/00; A61F 2/02; A61F 2/28
(52) U.S. Cl. .......... 424/423; 424/422; 424/423; 424/424; 424/425; 604/891.1; 501/1; 65/17.3
(58) Field of Search .................... 424/422, 423, 424/426; 65/17.3; 501/1; 604/89.11; 623/11, 16

(56) References Cited

U.S. PATENT DOCUMENTS

| | | | |
|---|---|---|---|
| 3,781,170 * | 12/1973 | Nakao et al. | 29/182.5 |
| 4,816,339 * | 3/1989 | Tu et al. | 428/421 |
| 5,204,106 * | 4/1993 | Schepers et al. | 424/423 |
| 5,480,438 | 1/1996 | Arima et al. | 623/16 |
| 5,762,950 * | 6/1998 | Yli-Urpo et al. | 424/422 |

FOREIGN PATENT DOCUMENTS 242 217 A1  1/1987  (DE).
WO 96/21628 * 7/1996 (WO).

* cited by examiner

Primary Examiner—Gollamudi S. Kishore
Assistant Examiner—Liliana Di Nola-Baron
(74) Attorney, Agent, or Firm—James C. Lydon

(57) ABSTRACT

A porous composite suitable for filling a recess or a through-passing hole in an implant. The composite includes particles A prepared from a bioactive material and particles B prepared from a non-bioactive material or weakly bioactive material, which is sintratable with the bioactive material, such that particles A and particles B have been sintered together to a porous composite. Particles A and particles B are essentially homogeneous in size. Also disclosed is an implant which contains a core and the composite.

14 Claims, 12 Drawing Sheets

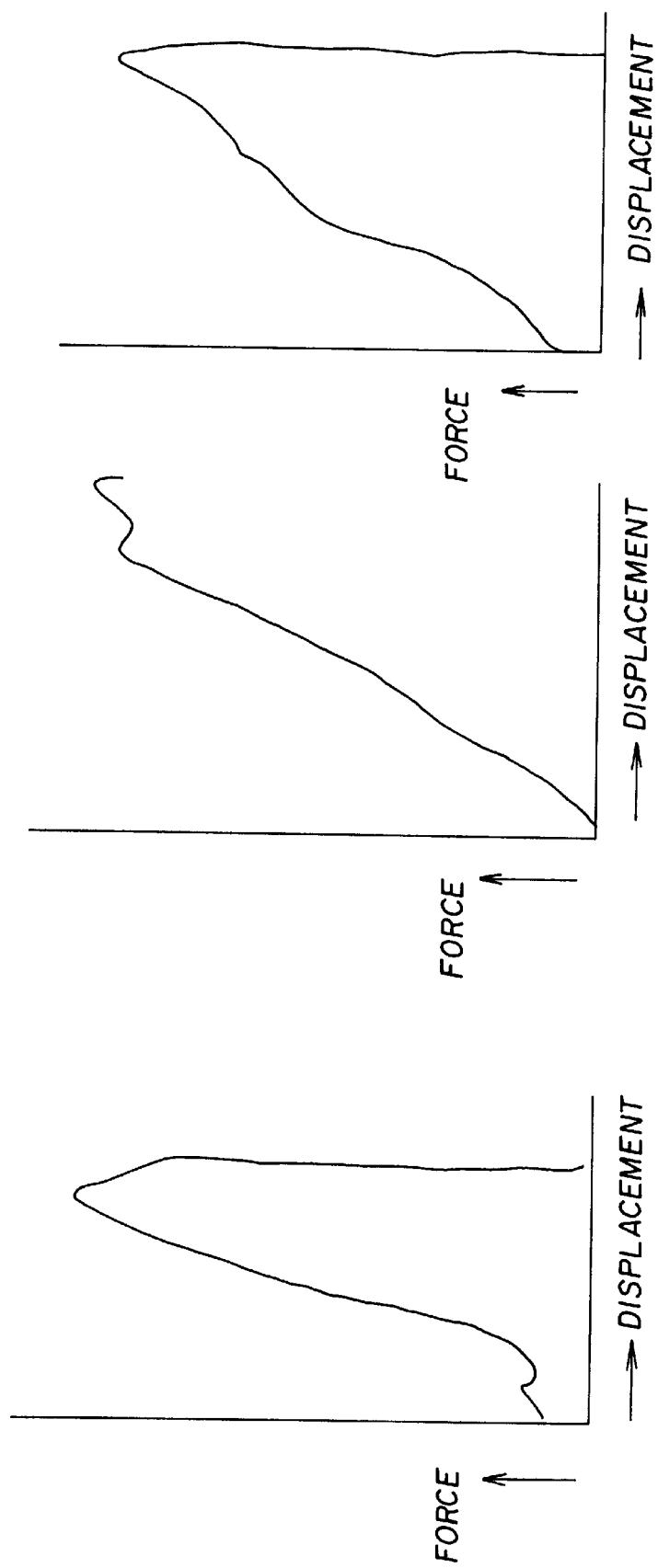

COMPOSITE AND ITS USE

This application is a U.S. national stage of International application PCT/FI98/00331, filed Apr. 15, 1998.

This invention concerns a porous composite as defined in the claim 1. The invention is also concerned with an implant comprising said composite.

GENERAL DEFINITIONS

The definitions below are to be understood herein as follows:

"Biomaterial" means non-living material, which is intended to be used in the body of a human or an animal. A biomaterial can be 1) inert, 2) bioactive, or 3) capable of bioresorption (solubilizable).

"Inert" means nonreactivity of the respective biomaterial with a tissue.

"A bioactive material" reacts in the physiological conditions within the body so that the outermost layer of a block manufactured from said material is converted to form a chemical bond with the surrounding host tissue.

An "osteoconductive" material means a material which facilitates the growth of newly forming bone along its surface but without giving rise to newly forming bone when introduced, for example, in muscle.

An "osteoinductive" material is generally a so called growth factor isolated from the interstitial matter of bone tissue or made synthetically, which induces the formation of newly forming bone for example in muscle.

An "implant" is any manufactured device of an artificial material, such as an artificial joint or a part of it, a screw, a fixation plate or a corresponding orthopedical or odontological device, which is to be introduced into a tissue.

"Host tissue" or "tissue" means bone tissue or soft tissue into which for example an implant has been surgically introduced.

"Micromotion" means microscopic motion (generally below 500 µm) within the interfacial region of a surgical implant and the host tissue caused by a dynamic load.

BACKGROUND OF THE INVENTION AND PRIOR ART

The publications, which have been referred to in order to illustrate the background of the invention and the prior art, are incorporated in the description of the invention below by reference.

Biomaterials and the biological anchoring thereof

Implants for both medical and odontological purposes have already been manufactured from various materials for a long time. Various metals, alloys, plastics, ceramic materials, glass ceramic materials and the newest or biologically active glasses are distinguished from each other not only by their durability but also by the properties of the interfacial layer between the implant and the tissue. Inert materials, such as metals and plastics, do not react with a tissue. In this case there always exists an interfacial layer between the implant and the tissue because the implant and the tissue form two distinct systems. Bioactive materials such as hydroxyapatite, glass ceramics and bioactive glasses react chemically with the tissue and produce a relatively strong chemical bond in the interface between the implant and the tissue, especially for the bioactive glasses. The implant and the tissue are thus anchored to each other. The rate of healing of the tissue and the potential chemical fixation to the implant is dependent on the activity of the implant material towards the tissue.

In designing the outermost layer of the implant it has to be considered that implants intended for functional activity are subjected to motion under a load immediately after the surgical operation. This compromises the healing and impairs the final result. In addition, the load is not communicated to the flexible bone by the structure of a non-elastic implant but the interfacial region in question is disturbed and the integration is blocked. Problems are often generated also by the lack of bone or the unacceptable quality thereof. If for example a dental implant is surgically placed into an insufficient or qualitatively unacceptable bone, the stability in the early phase is not attained and the surgical operation fails, if any bone is not generated beforehand. Under the functional conditions mentioned above, the undisturbed healing is not achieved with the currently used implants.

Specific Clinical Problems

1. Mechanical micromotions between the implant and the host tissue prevents the fast integration (osseal joining) within 6–12 weeks, in which case the device is left without a permanent firm anchorage to the surrounding tissue. The lack of this anchorage is known to lead to clinical detachment in an early phase (within 1–2 years) or even a number of years later and to the need of a repeat surgery (1), (2).

2. One approach is to have the surface of the implant made porous for example by means of a few millimeters deep three-dimensional surface structure constructed from microscopic titanium spheres or from titanium tape. Newly forming bone is expected to grow from the host tissue into this surface structure. Such a porous biologically inactive surface structure gives rise to a microscopic locking structure towards the ingrowing newly forming bone but the mechanical properties of this attachment do not allow a sufficient adaptation under the control imposed by the load conditions. The optimal anchoring structure between the implant and the host tissue is in a state of a continuous readaptation to make the strength of the structure to correspond to the load conditions.

3. It has been shown (3) that the attachment of a metallic bone implant (such as an artificial joint) to the host bone can be facilitated by a bioactive coating. The material used most often is synthetic hydroxyapatite. It has been demonstrated that hydroxyapatite 1) facilitates the mechanical attachment of an implant to the host bone after it has been attached firmly by means of a surgical operation, 2) diminishes the interference in the integration of the implant to the host bone caused by the micromotion, and 3) diminishes the retardation of the integration of the implant caused by local lack of bone and by the lack of contact to the bone implant. Hydroxyapatite is caused to attach to the surface of the implant by using a spraying technique, in which case the coating material is applied to the surface mostly only from the spraying direction. In the biomechanical and biological sense, the most optimal implant surface forms a three-dimensional structure, wherein the interstitial space of the structure forms a growth space to accommodate the ingrowing bone tissue. In such a case, healing leads to the formation of a connective locking structure. The growth of a newly formed tissue is facilitated, if the porous structure is entirely made of a bioactive material. In such a case the bioactive coating material forms a three-dimensional osteoconductive surface for the growth of newly forming bone. In exceptionally difficult conditions, where the growth of host bone is particularly poor for example because of low quality or small amount of the bone, the growth of the newly forming bone can optionally be improved by combining an osteoinductive component, which directly promotes the generation of bone, to a bioactive coating material.

Although a bioactive coating can improve the integration of the implant to the host bone, it must nevertheless be noted that this technique is associated with many problems. The combination of two materials which differ by their properties (elasticity, thermal expansion), is a technically demanding task. The coating of a metallic implant with a bioactive ceramic material can lead to the early breakdown of the coating, its fast corrosion, or slow detachment (delamination). This has shown to be the most common complication in efforts to use bioceramic materials, including hydroxyapatite, as a smooth coating material of metallic implants (4), (5) (6).

The optimal approach would be a construction which makes use of the advantages of a bioactive coating material to ensure early ossification but in which the possibility has been taken into account that the permanent integration can be secured by using other constructional approaches concerning the surface.

One problem with implants provided with bioactive coatings is also in that the bioactive surface, which is rather fragile, is damaged rather easily in the chasing of the implant into the bone.

OBJECTS OF THE INVENTION

One object of the invention is to provide a new composite, which when combined into the implant secures both rapid ossification and permanent integration of the implant.

Another object of the invention is to provide an implant, which allows the micromotion of the implant and the surrounding tissue (bone) and nevertheless secures rapid growth leading to the integration of the implant and the bone.

Still another object of the invention is to provide an implant which can be chased into the bone without a risk of damaging the bioactive structural component, which promotes the growth of a newly forming bone.

A further object of the invention is to provide an implant wherein the fracturability and the risk of detachment of the bioactive structural component are smaller than those of the known implants.

SUMMARY OF THE INVENTION

The invention is characterized by the independent claims.

Thus, according to one aspect, the invention concerns a porous composite, which is characterized in that is comprises:
   particles A manufactured from a bioactive material, and
   particles B, which are manufactured from a material which is non-bioactive or weakly bioactive and which is sintratable to the said bioactive material, and that the particles A and particles B have been sintered together to form a porous composite.

According to a further aspect, the invention concerns an implant which is composed of a core and a bioactive structural component which extends to the surface of the implant. The implant is characterized in that into the body has been made a recess or a through-passing hole which comprises the above mentioned composite according to the invention, said composite forming the surface layer of the implant at the recess or at the through-passing hole.

BRIEF DESCRIPTION OF THE DRAWINGS

FIGS. 11A–11C show push-out or detachment curves of the cones implanted into the bones in tests in vivo.

PREFERRED EMBODIMENTS AND DETAILED DESCRIPTION OF THE INVENTION

Figure 1A:
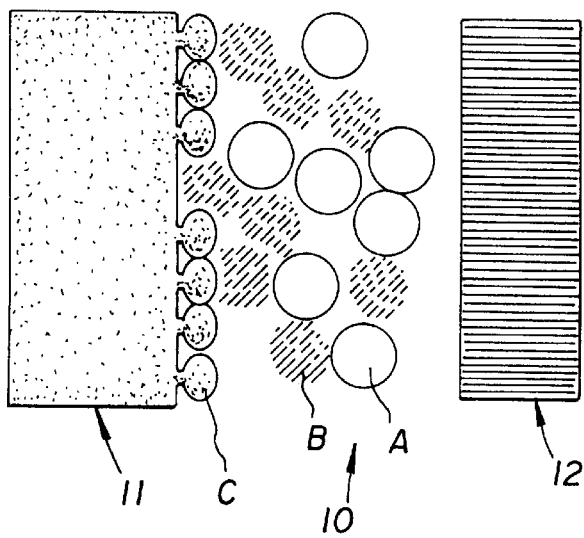
FIGS. 1A–1C show schematically tissue reactions of the composite according to this invention as a function of time.

In the definition of this invention, the bioactive material means a material which under the physiological conditions dissolves at least partly within a few months, most preferably within a few weeks, preferably in about six weeks. For example, a bioactive material can be a bioactive glass, a bioactive ceramic material or a bioactive glass ceramic material.

In the definition of this invention the term "non-bioactive or weakly bioactive material" i.e. the material from which the particles B have been prepared, means a material which under physiological conditions does not dissolve within the first few months. For example, this material can be a non-bioactive or weakly bioactive glass; a ceramic material, a glass ceramic material or hydroxyapatite. Thus, this material can be any physiologically acceptable material, the bioactivity of which is clearly lower than the material of the particles A and which additionally allows the particles A and particles B to be sintered together to form a porous composite. Particularly preferably, the non-bioactive or weakly bioactive material (the material of the particles B) begins to dissolve before the bioactive material (the material of particles A) has dissolved completely. In this case the superimposed formation of a chemical and mechanical bond between the tissue and the implant with respect to each other is best secured.

Preferably, the particles A and the particles B are essentially homogenous in size and approximately of the same size relative to each other.

Preferably, the diameter of the particles A and the particles B is in the range of 100–500 μm.

According to a preferred embodiment the particles are spherical, for example spheres manufactured by a torch spraying process wherein the raw material is glass. In such a case the particles A are made of bioactive glass and particles B of glass without or almost without bioactivity.

The problem with many traditional bioactive glasses is that they have poor workability because they easily crystallize. Such bioactive glasses cannot be manufactured into spheres.

The international patent application WO 96/21628 (7) describes new types of bioactive glasses, the working region of which is suited for the manufacture of glass and which thus allow the production of spheres. Typically, these glasses have the following composition:

$SiO_2$ 53–60% by weight
$Na_2O$ 0–34% by weight
$K_2O$ 1–20% by weight
$MgO$ 0–5% by weight
$CaO$ 5–25% by weight
$B_2O_3$ 0–4% by weight
$P_2O_5$ 0.5–6% by weight
provided that
$Na_2O+K_2O$=16–35% by weight
$K_2O+MgO$=5–20% by weight
$MgO+CaO$=10–25% by weight The above glasses are particularly suitable for use in this invention as the bioactive glass, i.e. as starting material for the particles A.

Preferably, the ratio of the amounts of particles A and B in the composite is adjusted so that the amount of particles A is 1/5 to approximately 1/1 of the total amount of the composite. A particularly suitable mixing ratio is one where the amount of particles A is about 1/3 of the total amount of the composite.

Of course, the composite of this invention can comprise particles of several bioactive materials and/or several non-bioactive materials or weakly bioactive materials.

Figure 1B:
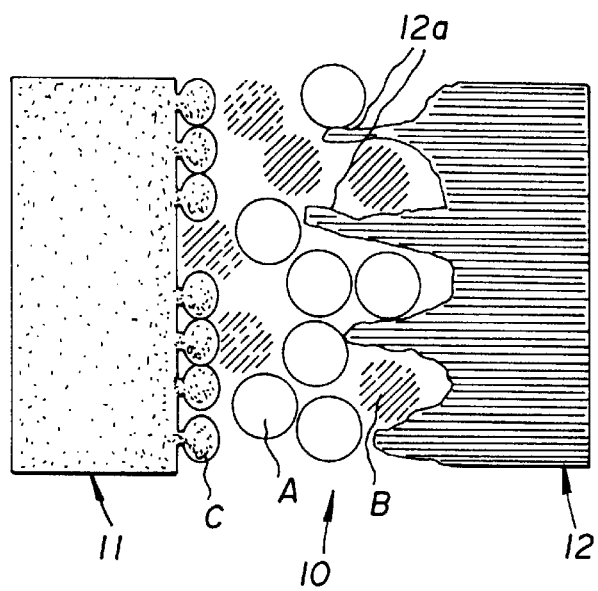
Figure 1C:
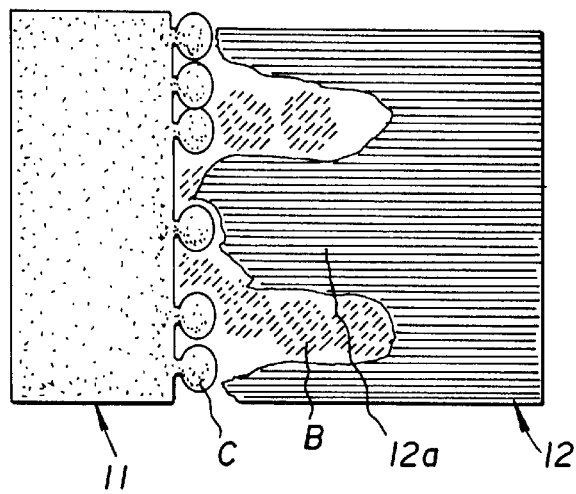

FIGS. 1A–1C show a tissue reaction of the composite according to this invention or a growing locking structure as a function of time. FIG. 1A represents a situation immediately following the surgical placement of the implant. Immediately next to the surface of the core 11 of the implant are positioned spheres C, which are composed, for example, of the same material as the core 11. A composite layer 10, which is composed of bioactive spheres A and spheres B, which are composed of non-bioactive or very weakly bioactive material, is left between the core 11 and the tissue (bone) 12. The spheres A and B are sintered together into a porous composite 10. FIG. 1B, which shows the situation after about 6–12 weeks, shows that newly formed bone 12a has grown into the pores formed by the spheres A and B. Said newly formed bone 12a forms together with the composite 10 a microscopic locking structure between the bone 12 and the core 11. FIG. 1C, which represents the situation months or years after placing the implant, shows a microscopic locking structure, wherein newly formed bone 12a and spheres B are found. The bioactive spheres A have been completely dissolved.

The series of FIGS. 1A–1C illustrates the formation of a chemical bond and a mechanical bond. Table 1 summarizes the amount of various bonds present.

TABLE 1

The types of bonds prevailing in FIGS. 1A–1C

|  | 1A | 1B | 1C |
| --- | --- | --- | --- |
| Chemical bond |  |  |  |
| Particle A → bone | – | +++ | – |
| Particle B → bone | – | ± | ++ |
| Mechanical bond | – | ++ | +++ |

Figure 2A:
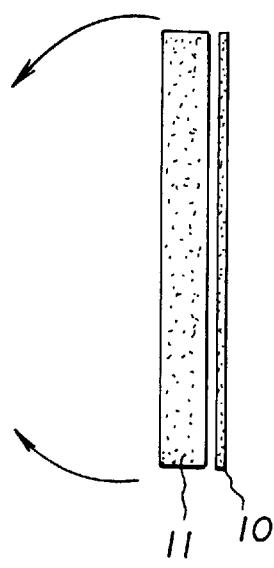
FIGS. 2A–2B show schematically the behaviour of the continuous and the discontinuous coating in the bending of the implant framework.
Figure 2B:
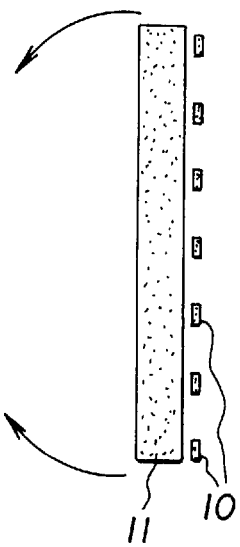

FIGS. 2A and 2B show a continuous coating 10 (FIG. 2A) and a non-continuous coating 10 (FIG. 2B) of the core 11, respectively. The bending of the core 11 in the case of FIG. 2A in the direction of the arrows results in a large ratio between the elongation of the coating 10 and the original length. Therefore, there exists the possibility that the above mentioned problems might be encountered. In contrast, when the core of FIG. 2B bends, the ratio between the elongation of the coating 10 and the original length is small. Thus the bioactive structural component functioning as a non-continuous structure retains its position much better.

Figure 3A:
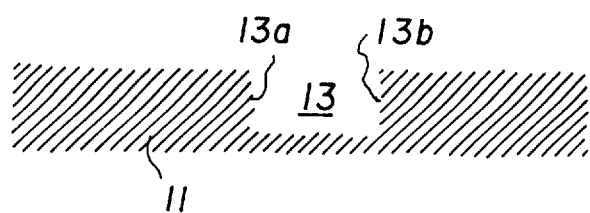
FIGS. 3A–3C show as cross sections the recesses made into the body of the implant.
Figure 3B:
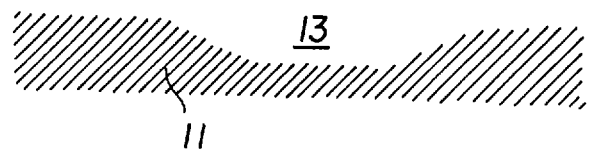
Figure 3C:
Figure 4:
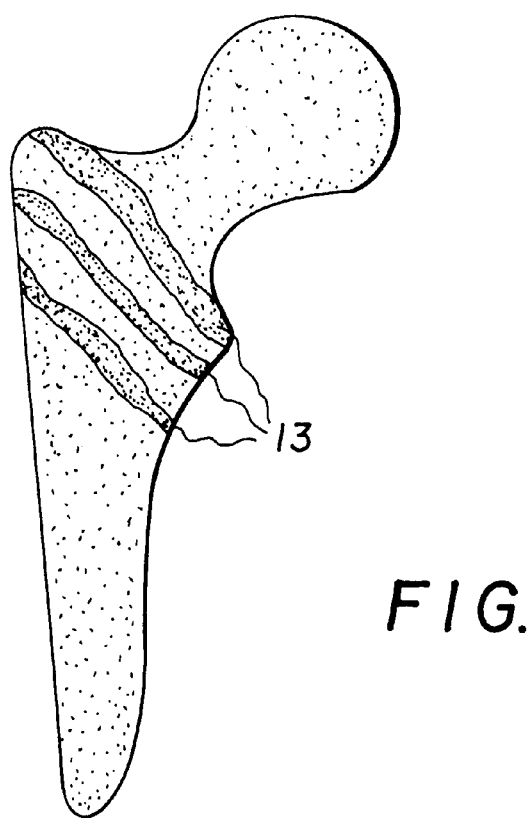
FIG. 4 shows a hip prosthesis, which has three recesses for the composite of the invention, FIG. 5 show as a cross section a recess made into the body of the implant, said recess being filled with a composite according to the invention, wherein the composite is comprised of distinct layers.

The implant according to this invention utilizes the principle of non-continuous coating. Into the core 11 of the implant are formed one or more recesses 13 (FIGS. 3–5) or a through-passing hole, and the composite according to this invention is applied into such recesses or holes. Thus, the composite will not cover the surface of the core as a continuous coating. Instead, the composite layer forms a layer 10 extending to the surface only at the recess or recesses 13 (or a hole or holes across the structure). FIG. 4 shows a hip prosthesis having three circular recesses 13 containing the composite according to the invention. FIGS. 3A–3C show examples of some profiles of the recesses. In FIG. 3A, the edges 13a and 13b of the recess are perpendicular to the surface of the core 13, in FIG. 3B the recess is widening outwardly, and FIG. 3C shows an outwardly closing or locking recess structure. The profile of the recess of FIG. 3C is particularly good because it secures the holding of the composite therein.

Figure 5:
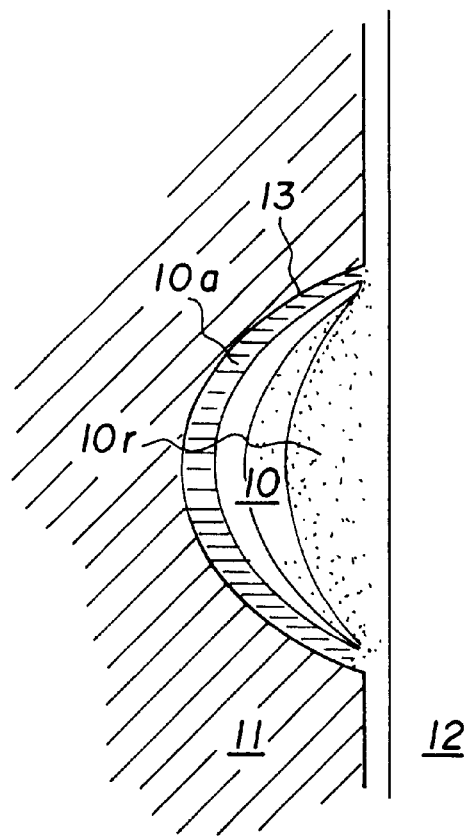

FIG. 5 shows an implant according to this invention wherein the composite layer 10 is composed of several sublayers 10a . . . 10n. The advantage with this structure is that the various sublayers can have a distinct mixing ratio between the particles A and B. The mixing ratios are preferably chosen so as to cause an increasing content of particles A in the composite from the innermost sublayer 10a towards the sublayer 10n in contact with the tissue 12. Particularly preferred is the composite layer 10 forming a gradient with respect to bioactivity.

Particularly preferred is an implant wherein the amount of the particles A in the sublayer 10a of the composite facing the interior of the core is 1/10 of the amount of the sublayer in question, and wherein the sublayer 10n to come in contact with the tissue is composed exclusively or almost exclusively of particles A.

In the approach of FIG. 5, if desired, inert particles preferably made of the material of the core can be sintered into the surface of the recess before the formation or the application of the composite into the recess.

According to one embodiment, the implant of this invention can be prepared so that the composite within a recess or in a through-passing hole is formed by applying the particles A and B into the recess, for example, as a mixture with an organic binding material. Sintering is then performed wherein the organic binding material is burned. If the composite layer is composed of several sublayers, the particles A and B required for each sublayer, respectively, are applied separately and sintered.

According to another embodiment the composite can be shaped into a block of the desired form and size capable of attaching to the recess or the through-passing hole in the inplant core. Such a composite block can be composed of several sublayers, in which case the different sublayers have a different mixing ratio of particles A and B so that the content of particles A increases from the sublayer facing inwardly into the implant core of the composite towards the sublayer of the composite in contact with the tissue.

By a proper selection of a narrow fraction and a suitable particle size and shape, the void space between the particles can be controlled so as to allow newly forming bone with its blood vessels to penetrate into the structure. When the ossification proceeds, the spheres prepared from, for example, a bioactive glass, are gradually resorbed. This generates more space for the bone, whereby the structure of the bone is strengthened. Therefore, the amount of the biomaterial is diminished as function of time. The diminution can be controlled by a proper selection of bioactive particles which are variable in their bioactivity and in their size and shape as well as by changing the mixing ratios of the various materials. In order to increase the durability of the final fixation of the bone, it is possible to use an inactive; porous structure made of the implant material in the bottom of the recesses. An essential feature of this surface, sintered for example from spheres, is its three-dimensionality. A conductive and inductive osseal contact is formed quickly. A coating made only by using bioactive glass (enamelling) would result only in the generation of a two-dimensional reaction surface and the healing would be more difficult.

By virtue of the bioactive material in the recesses an active healing reaction takes place already within a few weeks leading to a mature stage within a few months. This represents a noticeable improvement to the current situation, in which most of the failures are due to the fact that the fixation of the implant does not occur within the first six weeks.

The composite within the recesses of the implant is intended to function as a conductive, and in some applications inductive, surface for the rapid growth of newly forming bone and the chemical binding of the host tissue. The functions of recesses made into the implant core (or into the through-passing holes) can be summarized as follows:

The first object of the recess is to create for the bone tissue a healing process which is protected mechanically (from the mechanical micromotion). The static and dynamic load towards the implant and the consequent micromotion is thus not directly directed to the interface between the implant and the host tissue. This mechanically protected interface between the implant and the host tissue provides optimal conditions for the ossification and for the formation of a chemical bonding, in other words, undisturbed conditions are created for a fast integration of the device into the host bone.

The second object of the recess is to protect the surface material mechanically during the surgical placement of the implant. The implant can be affixed tightly to a pre-formed site (press-fit fixation) without causing a direct abrasive force to the bioactive material in the recess. The requirements upon the mechanical structural properties of the material can thus be less demanding.

The third object of the recess is to diminish the size of the uniform structure of the bioactive material. Especially for the enamellized material, the mechanical integrity is improved with the reduction in the size of the attachment region. Similarly, the coating of the whole circumference of the device is avoided, which contributes to the improvement of the mechanical integration durability of the bioactive material. Thus, the susceptibility of fracturing and the risk of loss of the bioactive structure is diminished.

The fourth object of the noncontinuous bioactive material placed into the recess, is to partly counteract the different elastic properties of the implant core and the bioactive material. The different elasticities of the materials can cause problems, for example, for keeping the bioactive structural component attached in the implant under different conditions of dynamical load.

The fifth object of the recess is to create a macroscopic surface structure for the locking of the newly forming bone, which surface structure in itself strengthens the mechanical bonding of the implant due to the ingrowth of newly forming bone. The inclined locking structure (FIG. 3C) provides a macroscopic locking structure between the host tissue and the device.

A porous surface structure which is unreactive (non-bioactive) with the tissue can be formed on the bottom of the recess. This surface structure fulfils the function of creating, when needed, a microscopic three-dimensional mechanical locking joint between the device and the bone tissue, based on the growth of the newly forming bone. The object of this bottom structure is to secure a permanent mechanical bone junction between the implant and the host tissue in those cases where the bioactive coating structure has completely eroded. A second object of the bottom structure is to cover those bearer regions where the use of a bioactive component is unwanted but which are needed to secure the circular fixation of the device in the wanted direction.

Figure 6A:
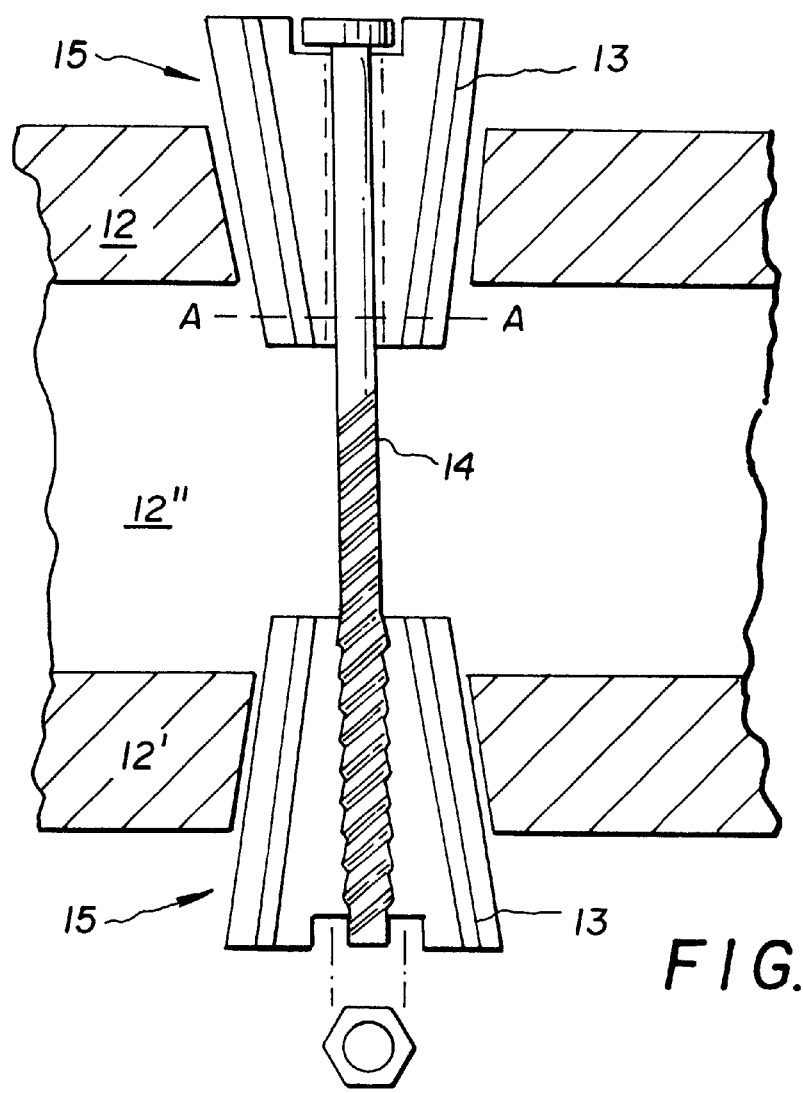
FIGS. 6A–6F show the use of the composite according to this invention in joining and bone screws.
Figure 6B:
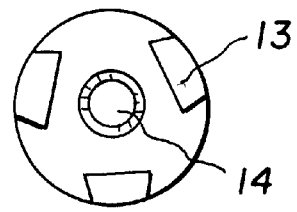
Figure 6C:
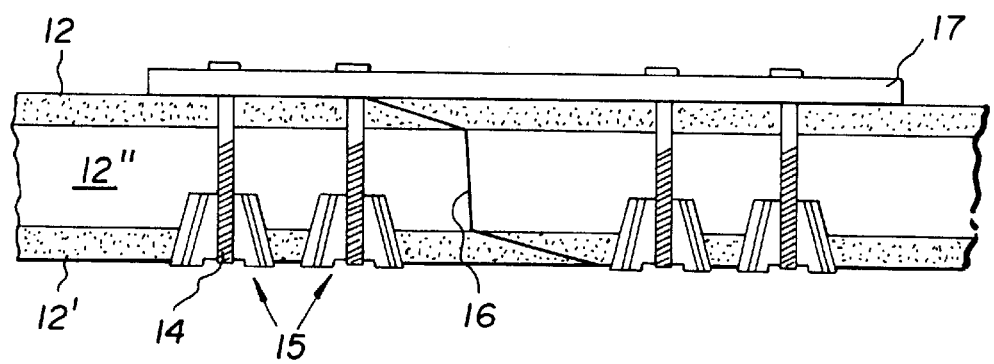

An example of other applications is a tightening joining screw for various orthopedical operations to the bone as shown in FIG. 6A. The approach of FIG. 6 is suited particularly for osteoporotic bones. In this application the joining screws 14 are fixed into the bone with separate, for example cone-shaped devices 15 having recesses 13, which in themselves comprise material causing bioactive ossification. The bioactive agent (or bioactive agents) are attached to the surface of the device according to the method described above. The reference numbers 12 and 12' denote bone and the number 12" denotes marrow. FIG. 6B shows a cross section of the conical device 15 along the line A—A of FIG. 6A. FIG. 6C shows a plating operation of a fracture 16 of an osteoporotic hollow bone 12 and 12', wherein the metallic plate has been given the number 17.

Figure 6D:
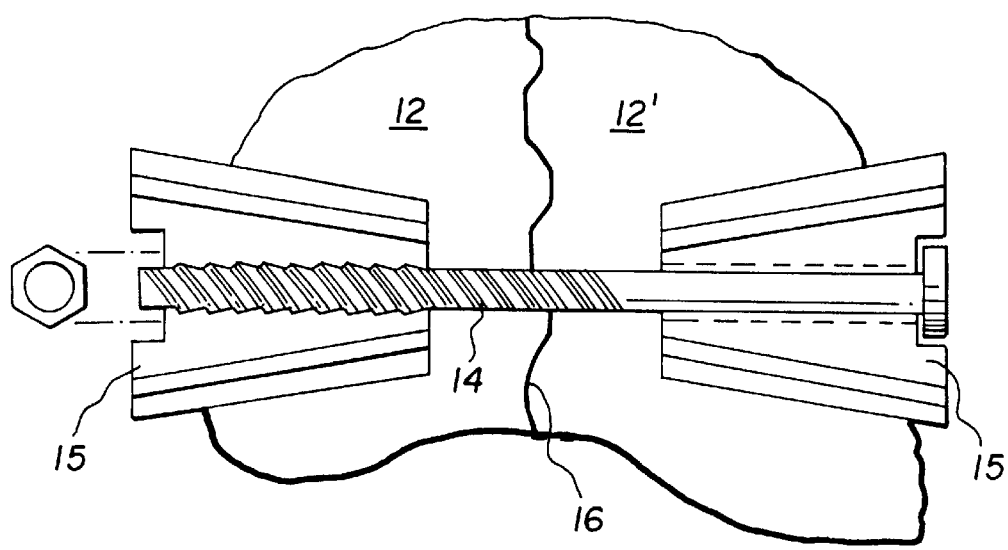

FIG. 6D shows the fixation of a fracture 16 of the navicular of the wrist by using the tightening joining screw described above.

Figure 6E:
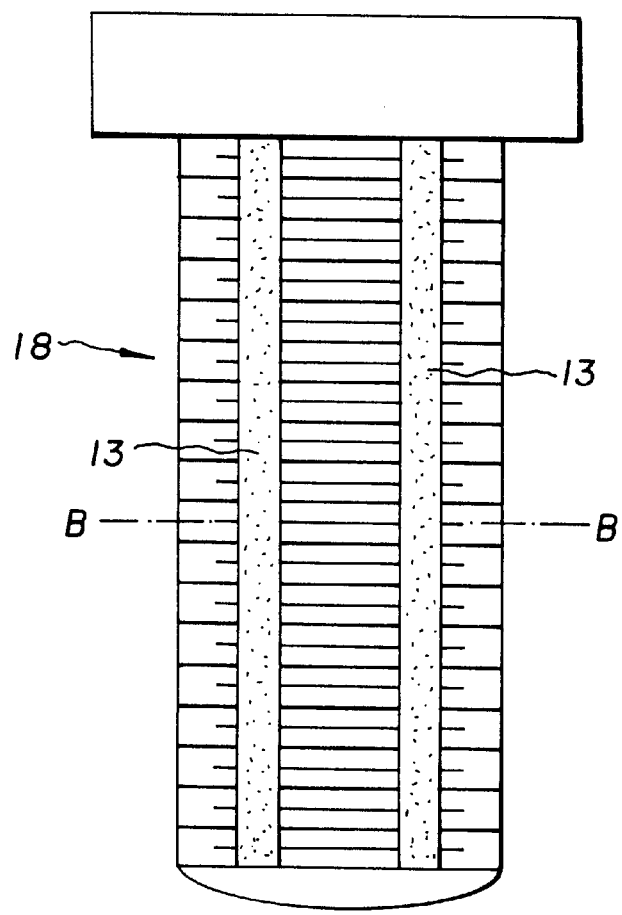
Figure 6F:
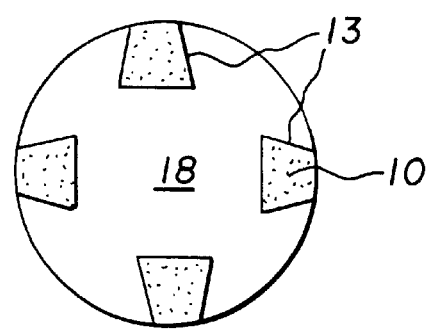

An another application is, as illustrated in FIG. 6E, an ordinary bone screw 18, which has recesses 13 made for the bioactive material 10. FIG. 6F shows a cross section of a bone screw along the line B—B of FIG. 6E.

EXAMPLES

Example 1

Preparation of the Glasses

For the experiments described below, two types of glasses were prepared of which a was bioactive and b was very weakly bioactive. The glasses were prepared by mixing a paste from PA (pro analys) grade raw materials. The raw materials were $Na_2CO_3$, $K_2CO_3$, $MgO$, $CaCO_3$, $CaHPO_4*H_2O$, $H_3BO_3$ and fired $SiO_2$. The composition of the prepared glasses is given in Table 2.

TABLE 2

The composition of the prepared glasses (weight-%)

| Glass | $Na_2O$ | $K_2O$ | $MgO$ | $CaO$ | $P_2O_5$ | $B_2O_3$ | $SiO_2$ |
|---|---|---|---|---|---|---|---|
| a | 6 | 12 | 5 | 20 | 4 | — | 53 |
| b | 25, 5 | — | — | 11 | 2, 5 | 1, 3 | 59, 7 |

After weighing and mixing, the paste was melted in a platinum crucible at a temperature of 1360° C. with a melting time of 3 hours. The glass melt was casted in a graphite mould into blocks which were cooled at 520° C. for 30 minutes and subsequently in the oven, which was left to cool after switching the power off. The finished glasses were crushed and melted again in order to homogenize the glass mass. The glasses, which had been re-casted and cooled, were crushed and sieved into the 250–297 µm fraction, whereafter the sieved crush was treated with a magnet to remove the small iron particles detached during the crushing operation.

Example 2
Preparation of Glass Spheres

Using a torch spraying technique, the small glass particles were heated for a short time to a sufficient degree to have them melted and become rounded by virtue of the surface tension. After a quick cooling, the glass spheres were collected into a receptacle.

The torch spraying device used in the experiments comprised of a container for the crushed glass, a feeding tube, a common input head for the gases and crushed glass, and a nozzle. A mixture of acetylene and oxygen was used for heating. The nozzle was Castodyn 8000 nozzle nr. 30, which is intended for ceramic spraying. This nozzle gives a sufficient heat to round even the largest particles. The crushed glass flowed into the nozzle from the container above the device by its own weight. After a suitable mixing ratio has been found, the different quantity of heat required for the melting of different fractions can be controlled by adjusting the flow rate of the gases. Smaller particles melt faster than the larger ones and thus necessitate passing through the flame at a greater velocity, that is a greater flow rate of the gases. A suitable gas flow for the fraction 250–297 µm was 4 $dm^3$/min for acetylene and 6 $dm^3$/min for oxygen. A funnel made of stainless steel with a glass container below was used to collect the glass spheres.

In order to assure a good quality of the glass spheres, sieving (ø 250–297 µm), magnet treatment and light microscope checking were performed immediately after the preparation. After ultrasonic washing in ethanol, the spheres were stored in ethanol in a closed vessel.

Figure 7:
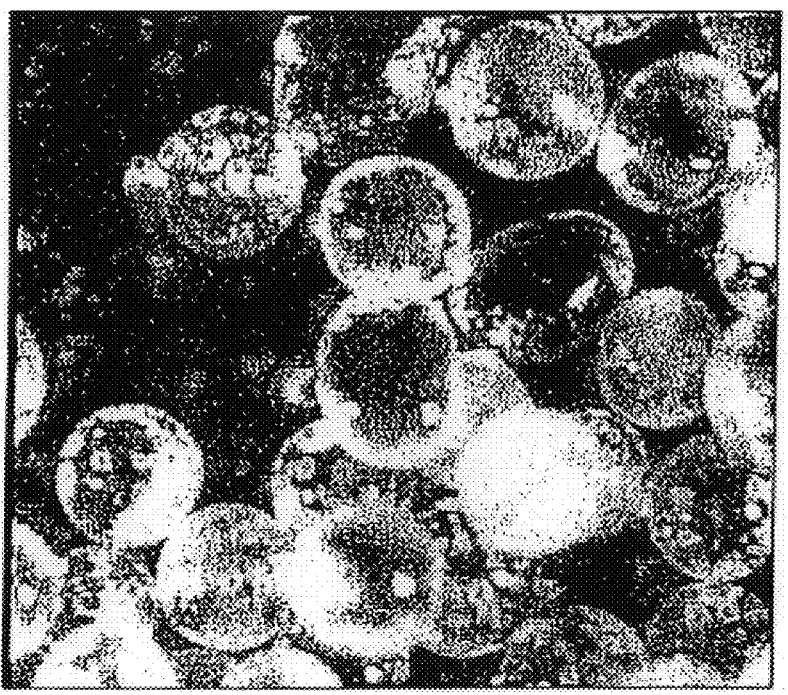
FIG. 7 shows a light micrograph of glass spheres manufactured by using a torch spraying technique.

FIG. 7 shows a light micrograph of glass spheres (ø 250–297 µm) manufactured by torch spraying technique. The glass speres had been prepared of bioactive glass (glass a, Table 2).

Example 3
Preparation of Glass-Based Cones

The implants used in the experiments described below were prepared by sintering glass spheres prepared according to the previous example into porous devices having the shape of a truncated cone. For the preparation of the glass cones, the glass spheres prepared from the glasses a and b of Table 2 were used. Two types of glass cones were prepared, type I and type II. The first type (I) of glass cones was prepared by sintering glass spheres which were torch sprayed from the glass a of Table 2. The second type (II) of glass cones was prepared by sintering a mixture of glass spheres of which ⅓ were glass spheres prepared from the glass a of Table 2 and ⅔ glass spheres prepared from the glass b of Table 2.

Figure 8A:
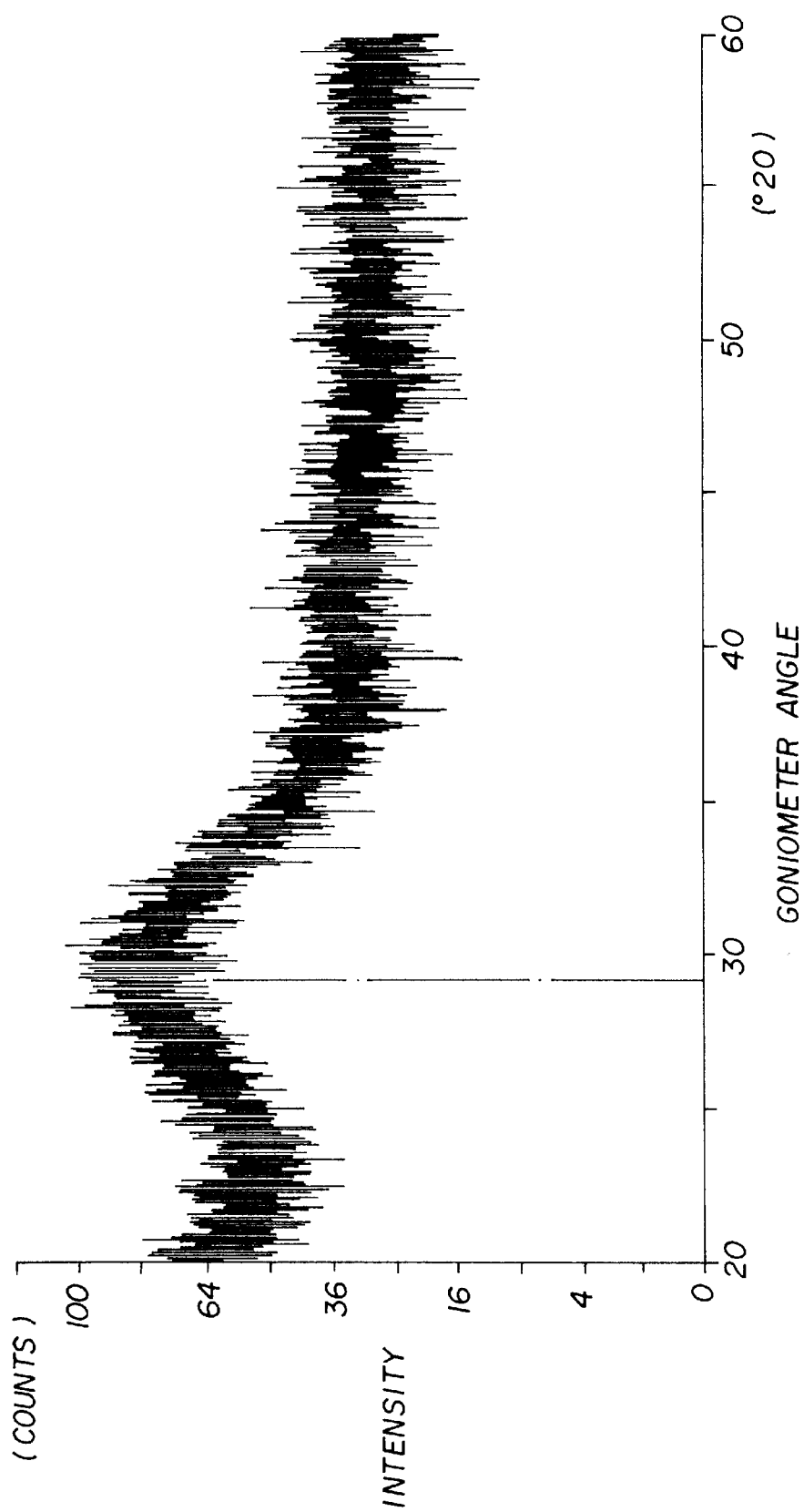
FIGS. 8A–8C show X-ray diffractograms of finely-ground glass-based cones.
Figure 8B:
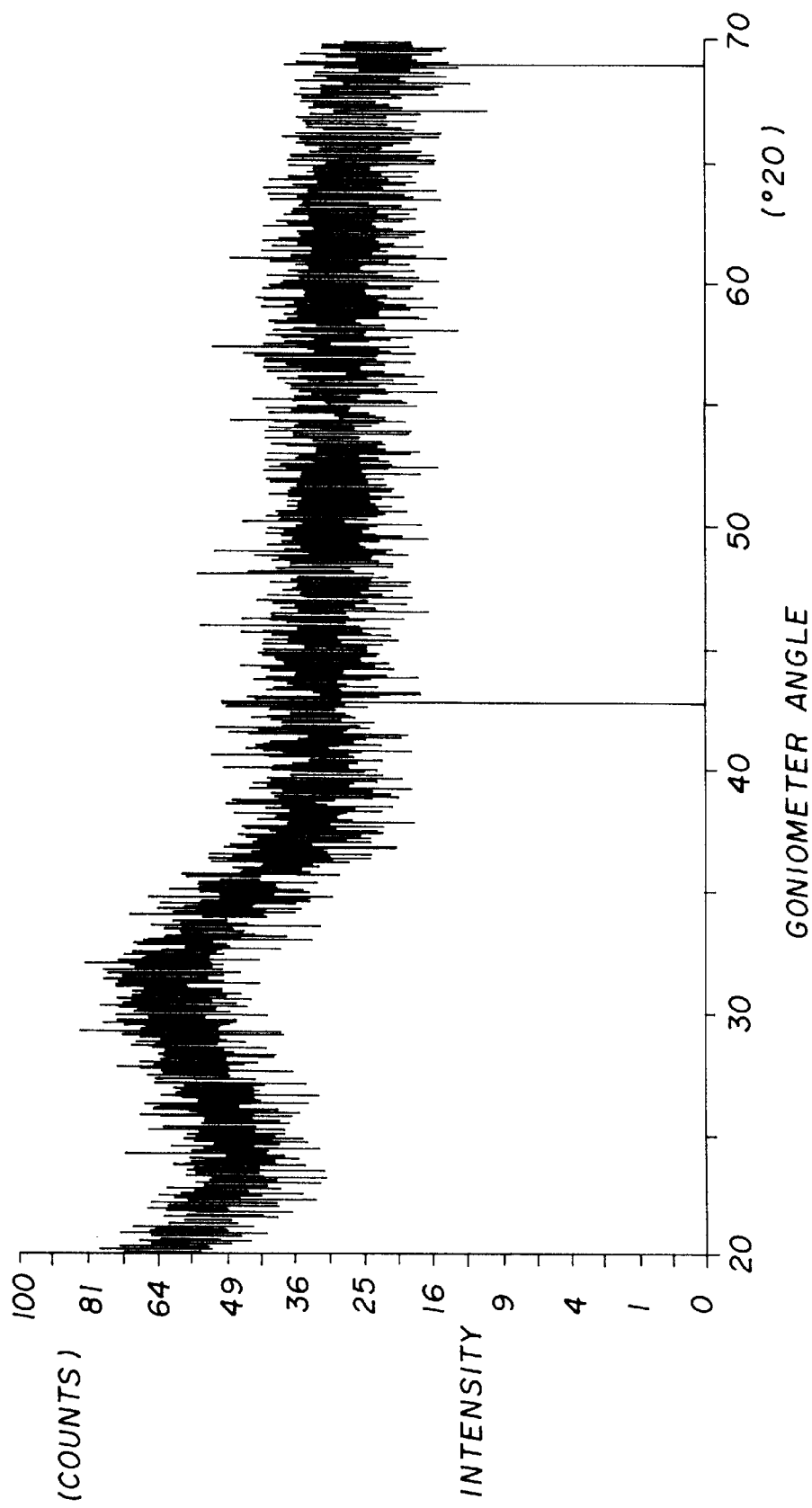
Figure 8C:
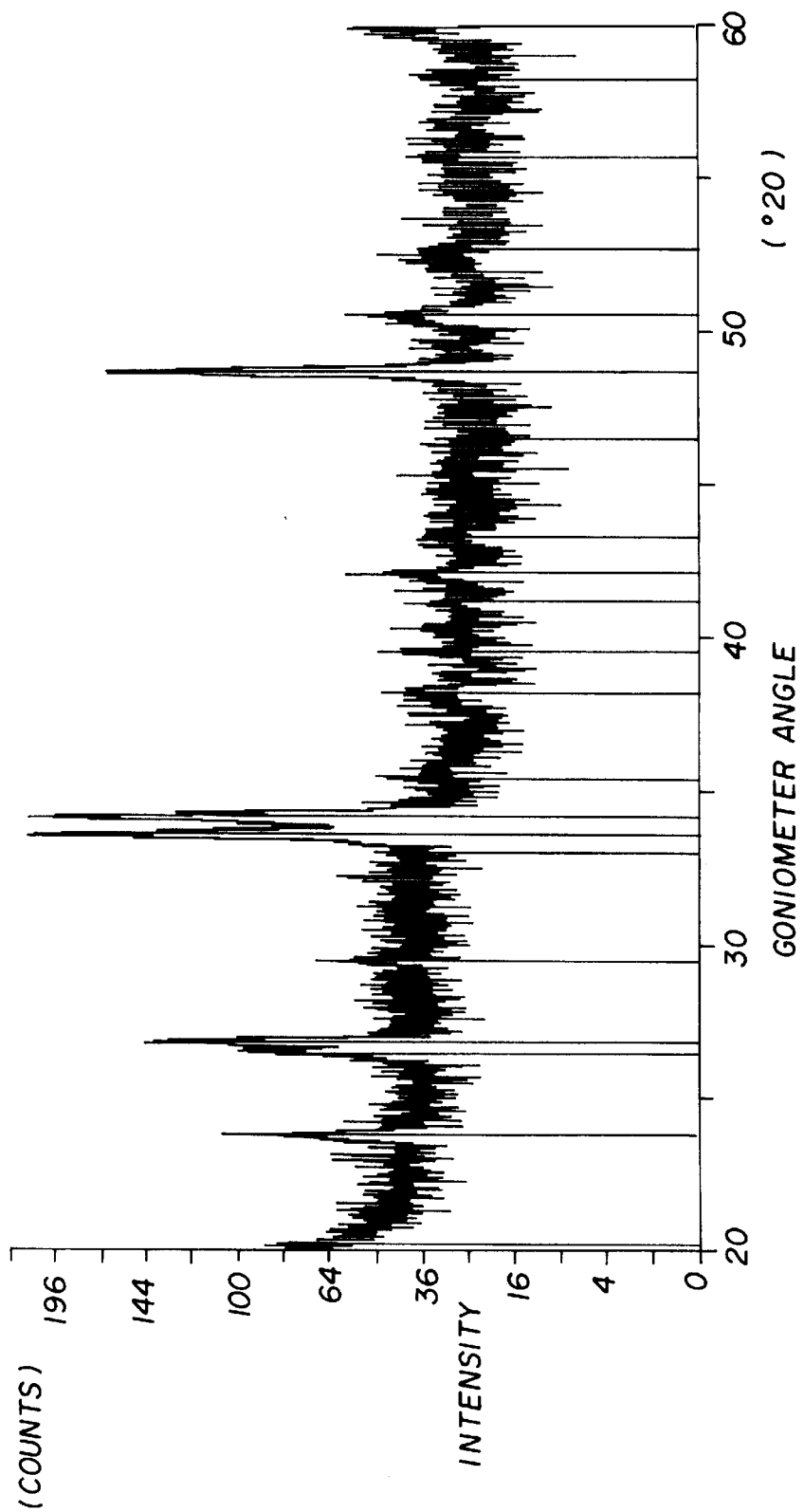

FIGS. 8A and 8B show an X-ray diffractometric analysis of a randomly chosen crushed cone. FIGS. 8A and 8B are X-ray diffractograms of the cone type I and the cone type II, respectively. It can be seen from these Figures that the glass has retained its amorphous structure after the heating processes associated with the preparation of the cones. FIG. 8C shows an X-ray diffractogram of a control cone, wherein the observed peaks demonstrate the occurrence of crystallization in the glass structure. The control cone was prepared from glass spheres, for which a conventional bioactive glass, in other words glass without potassium or magnesium oxide, was used as a raw material.

For the sintering a rectangular mold (50×30×20 mm) was prepared from graphite, into which ten 14 mm deep holes were made using a cone-shaped 4 mm bit. The holes were filled with the prepared glass microspheres, and the mold with the spheres was heated in a preheated Naber L 49 oven.

Both of the cone types I and II were prepared at the sintering temperature of 760° C. The sintering time for the cone type I was 5 min 15 s and the sintering time for the cone type II was 3 min 40 s.

The cones which were overshrinked (overmelting) during the heating were discarded and the accepted cones were checked for the thickness of the necks between the spheres by using a light microscope. The length of the cones was 14 mm and the ø=2.9 mm and 3.9 mm. The finished cones were washed in ethanol by using an ultrasonic treatment and stored in ethanol in a closed vessel.

Figure 9:
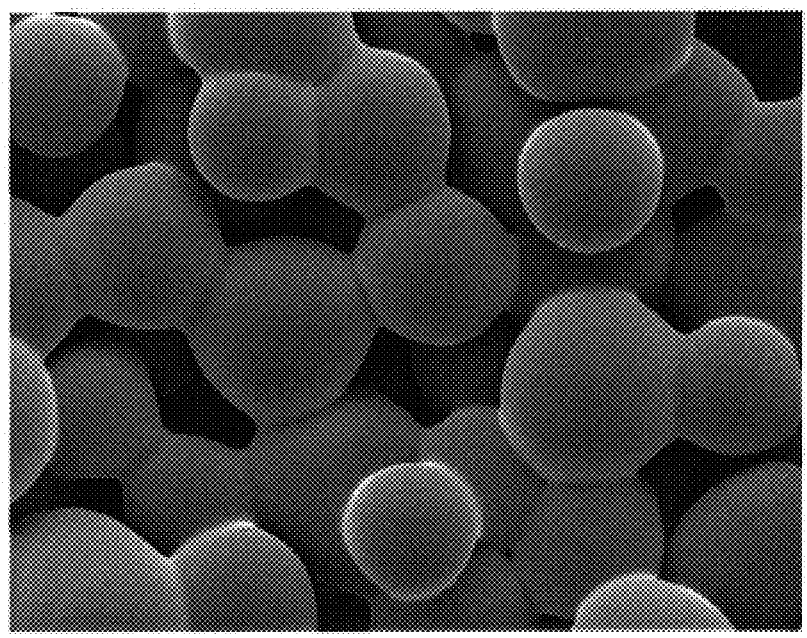
FIG. 9 shows a scanning electron micrograph showing bioactive glass spheres sintered together.

FIG. 9 represents a scanning eletron micrograph, which shows bioactive glass spheres of type I sintered together ø=250–297 µm.

Example 4
Preparation of Titanium-Based Cones

For comparison, a titanium-based cone type was prepared by sintering titanium microspheres. Microspheres prepared from medical grade titanium by atomizing in a protective argon gas were purchased from Comp Tech, Tampere. The spheres were sieved to a fraction 250–297 µm and washed ultrasonically in ethanol. Because titanium reacts very easily with oxygen at higher temperatures, the sintering of titanium must be done in a vacuum oven. For the sintering, molds resembling the ones used in Example 3 were prepared by drilling holes with a 4 mm cone-shaped bit into a graphite block. The blocks were filled with titanium microspheres and the sintering was performed in a vacuum oven at a temperature of 1500° C. and with a sintering time of 2 h 30 min. A successful result was checked after the sintering by using a light microscope.

Figure 10:
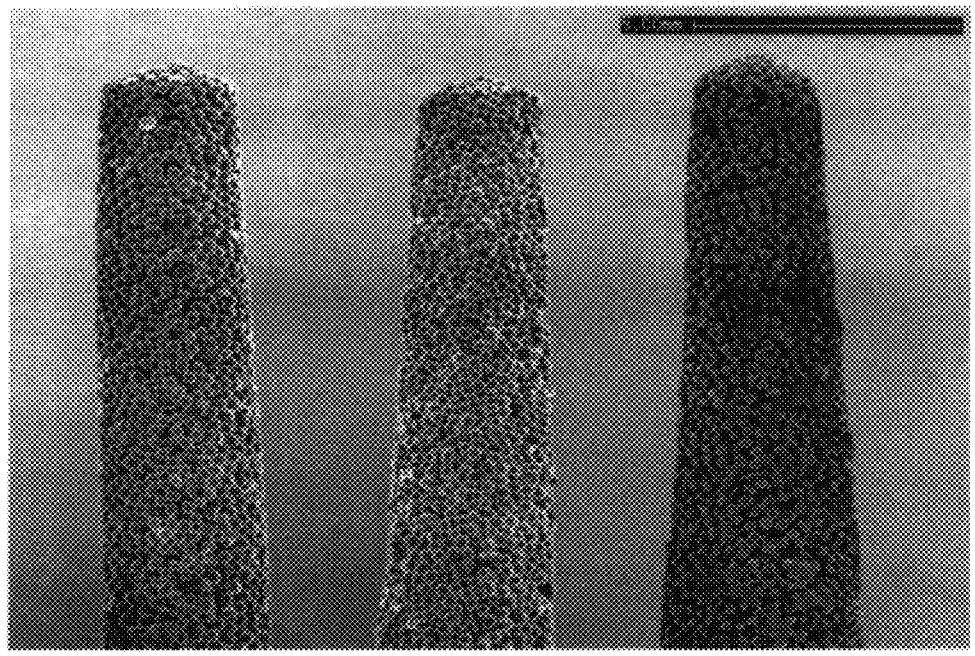
FIG. 10 shows implant cones used in tests in vivo.

FIG. 10 represents cones used as implants in this study. The cone shown on the right represents the glass cone type I and the cone shown in the middle the glass cone type II from Example 3. The titanium-based cone described above is shown on the left. The spheres have a ø=250–297 µm.

Test Results

The durability of the sintering necks observed in FIG. 9 is influenced essentially by not only the behaviour of the glass in the tissue but also by the successfulness of the sintering. The sintering result, i.e. the mechanical strength of the matrix, is compromised by the sintering of more than one type of glass together. This is due to the fact that different glasses have different coefficients of thermal expansion; during the cooling, microfractures develop in the structure of the matrix. In order to clarify the differences in the mechanical strength of the different matrices, a mechanical compression test was performed on the cones made of glass spheres.

1) Compression strength of the cones

For the compression test, blocks with dimensions corresponding to those of the types I and II of the cones made of glass spheres, respectively, were prepared by sawing off the excessive material from the both ends, in which case the cone block to be tested was 4 mm in length, ø=3.3 and 3.4 mm, respectively. The compression strength of the titanium cones was not measured, because the strength of the sintered titanium cone would have exceeded the maximum load of the measuring device.

The measuring device was composed of an Alwerton compression device and a recorder. In the device, a downward-moving probe proceeding at a constant velocity compresses a block on a solid platform. The velocity can be controlled and the probe measures the load upon the block. The device is connected to a recorder and this is arranged to record the maximum load before the disintegration of the block.

The compression strength of the cones made of glass spheres is shown in the Table 3.

TABLE 3

| Glass cone type | Number of tests | Compression strength (MPa) |
| --- | --- | --- |
| I | 8 | 17, 5 ± 3, 9 |
| II | 7 | 5, 0 ± 1, 0 |

2) Push-out test of the cones

Into the femur of rabbits (n=8) were implanted cones, which represented the glass cone types I and II described in Example 3, and the titanium-based cone type described in Example 4. A similar series of three cones were implanted into both femurs, one for histomorphological determinations and the other for biomechanical determinations. The total number of implants was 3×16=48 cones. After a six week follow-up period, the rabbits were sacrificed, the femurs removed and the force (the push out force) needed for the detachment of the cone from the bone was determined.

The biomechanical push-out test was performed on the same device as the compression strength test described above. For the test, the ends of the femur were cut and the bone was split longitudinally. The excess part of the implant inside of the bone was removed and the exterior of the bone was carefully cleaned. The bone was then placed against a solid support. The support had a central hole with dimensions suitable for fitting the other end of the detaching cone. The device was switched to register the maximal load, the compression rate was 0.5 mm/min. In addition, the device was connected to a recorder with a paper velocity of 30 mm/min.

A summary of the results of the push-out test is shown in Table 4.

TABLE 4

The push-out force needed for the implanted cones after a six week tissue reaction

| Cone type | Number of tests | Push-out force (N) |
| --- | --- | --- |
| Glass cone type I | 8 | 216, 2 ± 20, 6 |
| Glass cone type II | 8 | 293, 3 ± 43, 8 |
| Titanium-based | 8 | 230, 6 ± 15, 4 |

Given that the contact surface to the bone was the same for all of the cones (the depth of hard bone=1 mm=the height of the cone) the push-out strength was calculated by dividing the push-out force by the contact surface of the cone. The push-out strength is shown in Table 5.

TABLE 5

The push-out strength of the implanted cones after a 6 week tissue reaction

| Cone type | Number of tests | Push-out strength (MPa) |
| --- | --- | --- |
| Glass cone type I | 8 | 20, 8 ± 2, 0 |
| Glass cone type II | 8 | 28, 3 ± 4, 2 |
| Titanium-based cone | 8 | 22, 2 ± 1, 5 |

FIG. 11 shows the push-out curves for the different cones, wherein the push-out force is expressed as a function of dislocation (11A=glass cone type I, 11B=glass cone type II, and 11C=titanium-based). The slopes of these curves can be used to calculate the so called push-out stiffness, which is a ratio:
push-out force/dislocation
and which describes the stiffness of the implant core during the push out test. The push-out stiffnesses for the different cones is given in Table 6. The stiffness of the matrix is directly proportional to the slope of the curve.

TABLE 6

The push-out stiffness of the implanted cones after a 6 week tissue reaction

| Cone type | Number of tests | Push-out stiffness (N/mm) |
| --- | --- | --- |
| Glass cone type I | 8 | 301, 6 ± 150, 6 |
| Glass cone type II | 8 | 214, 5 ± 99, 4 |
| Titanium-based cone | 8 | 277, 4 ± 149, 2 |

Discussion

Testing of the cones made of glass spheres

The matrix sintered from two different types of spheres allows the combinatory sintering between the spheres of three different types: a—a, a—b, and b—b. Because the glasses differ by their coefficients of thermal expansion, the necks a—b are weak or partially broken (tensioned) after cooling. Only the necks between the two similar glasses are strong and these are mainly responsible for the mechanical strength of the matrix.

The test results of the compression strengths of the cones made of glass spheres (Table 3) demonstrate that the matrix sintered from microspheres prepared from two different glasses is notably weaker than a matrix of spheres prepared from a single glass. It can be supposed that all the necks in a matrix of spheres prepared from a single glass are intact after cooling. The strength of the matrix sintered from a mixture of glass spheres (glass cone type II) is improved if the ratio between the a/b spheres is diminished, or the fraction of the spheres prepared from the bioactive glass (a) is reduced. In this case the mixture of the spheres is made more homogenous and the number of necks is increased. In this study the ratio $1/3$ was used.

The behaviour of the implanted cones in vivo

1) Cones sintered from the bioactive glass spheres (glass cone type I)

In connection with the implanting of the cones it was possible to observe immediately the fast penetration of bone marrow fluid into the cone matrix. The matrix was, due to the capillary force, filled completely with tissue fluid and blood, so that there was a plentiful amount of reaction surface between the glass and the tissue/tissue fluid.

The bioactive glass reacts with all of its surface, in which case all the necks are solubilized with time. This leads gradually to the weakening of the matrix with the onset of breaking of the necks.

In the push-out test, which was made after a six-week tissue reaction, it is observed that the cones sintered from bioactive glass are attached to the bone rather strongly. In spite of the essentially weaker core, the push-out strength (20.8±2.0 MPa) is approximately of the same order of magnitude as the push-out strength (16–23 MPa) measured for a cone molded from a bioactive glass in previous studies (8). This can be explained by the ingrowth of newly forming bone into the matrix. Concurrently with the growth of bone into the cone, the bioactive glass is solubilized and the matrix as a whole is weakened. At the maximal load of the push-out value the considerably weakened necks break near the outer edge of the cone and the cone is displaced as the newly ingrown bone yields at the edges of the cone. The abrupt rupture of the bond between the implant and the bone is also illustrated by the so called push-out stiffness of the cone sintered from bioactive glass spheres (301.6±150.6 N/mm), which is of the same order of magnitude as the cone sintered from titanium spheres (277.4±149.2 N/mm).

2) Cones sintered from a mixture of glass spheres (glass cone type II)

The tissue reaction of this cone type begins vigorously only on the surface of the bioactive spheres. In contrast, spheres prepared from very weakly bioactive glass (b) react or dissolve very slowly. Newly forming bone has the opportunity to grow into the pores as induced by the bioactive component. However, mainly the bioactive component dissolves from the matrix with time and the spheres prepared from glass b remain as a support for the core.

The push-out test shows clearly the push-out strength (28.3±4.2 MPa) as compared to the corresponding figure for the cone type I or the titanium-based cone (approximately 22 MPa). Similarly, the push-out stiffness (214.5±99.4 MPa), which illustrates the stiffness of the core, demonstrates that the core is more flexible by virtue of the remaining matrix composed of the remaining intact glass type b which provides support for the core. The stiffness of the cone sintered from the mixture of spheres is clearly smaller than the corresponding figure for the cones sintered from the bioactive glass spheres or the titanium spheres. The structure of the core is markedly more heterogenous than in the cones sintered from only one type of glass spheres. The newly formed bone grown into the pores gets support in the push-out process from the remaining matrix composed of the glass type b, in which case the bonding between the bone and the cone becomes markedly more durable and more flexible than the bonding between the cones sintered from only bioactive glass spheres or titanium spheres and the bone. The large standard deviation in the push-out strength and in the push-out stiffness is explained by the different compositions of the individual cones prepared from the mixture of spheres (which again results from the fact that the mixture of spheres from which the various cones were sintered, was not completely homogenous). Thus the durability of the matrix is variable.

3) Cones sintered from titanium microspheres

Titanium is an inert material used widely in surgical implants. The bonding between the implant and the tissue is good but there is no bonding at the interface. In studies performed previously (8) it has been shown that the push-out strength of a smooth titanium cone (approximately 2 MPa) is considerably inferior when compared with the strength of a corresponding cone molded from a bioactive glass (16–23 MPa). In this study the push-out strength of a cone sintered from titanium microspheres (22.2±1.5 MPa) was about ten-fold as compared to the corresponding strength of the smooth titanium cone measured in the above-mentioned reference and of the same order of magnitude as the push-out strength of a cone sintered from bioactive glass spheres. The increased strength of a porous titanium cone results from not only the coarseness of the interface but apparently also from the implant-supporting influence of the newly formed bone grown into the implant matrix. At the time of detachment the bone strings at the interface are broken and the cone is detached. The push-out stiffness (277.4±149.2 N/mm) is of the same order of magnitude than the push-out stiffness of the cones sintered from bioactive glass spheres and markedly larger than that of the cones (214.5±99.4 N/mm) prepared from the mixture of the spheres. The matrix sintered from titanium spheres can not even be supposed to be flexible.

The composite according to this invention can be used to facilitate the bonding of any orthopedical (medical or veterinary) or odontological implant.

The above mentioned embodiments of this invention represent merely examples of the application of the idea of this invention. It is evident to the one skilled in the art that the various embodiments of this invention can be varied within the scope of the following claims.

References

1. Freeman M A R, Plante-Bordeneuve P: "Early migration and late aseptic failure of proximal femoral prostheses". J Bone Joint Surg 76-B:432–438, 1994.
2. Karrholm J et al., "Does early micromotion of femoral stem prostheses matter?" 4–7-year stereoradiographic follow-up of 84 cemented prostheses. J Bone Joint Surg 76-B: 912–917, 1994.
3. Jaffle W L, Scott D F: "Total hip arthroplasty with hydroxyapatite-coated prostheses". J Bone Joint Surg 78-A:1918–1934, 1996.
4. Ducheyne P, Cuckler J: "Bioactive prosthetic coatings". Clin Orthop 276:102–114, 1992.
5. Ido K et al., "Cementless total hip replacement. Bioactive glass ceramic coating studies in dogs". Acta Orthop Scand 64:607–612, 1993.
6. Pajamäki J: "Bioactive glass and glass-ceramic interfacial reactions to bone". Acta Univ Tamperensis vol 406, 1994.
7. Brink et al., WO 96/21628.
8. Ö. H. Andersson et al., "Evaluation of the acceptance of glass in bone", J. Mater. Sci.: Mater. in Medicine 3(1992) 145–150.

What is claimed:

1. A porous composite, which is intended to be filled into a recess or a through-passing hole of an implant, and which comprises:

particles A prepared from a bioactive material which will react in the physiological conditions within the body so that an outermost layer of a block of said bioactive material forms a chemical bond with surrounding host tissue, and particles B, which are prepared from a non-bioactive material or from a weakly bioactive material which under physiological conditions does not dissolve within the first few months, wherein the particles A and the particles B are partially melted together to form a porous composite having a three dimensional structure in which individual particles are connected to at least one adjacent particle but retain a substantially spherical individual shape, characterized in that the particles A and B are essentially homogeneous in size, and wherein said particles A and particles B are approximately the same size compared to one another, and have a diameter of at least 250 microns.

2. The composite according to the claim 1, characterized in that the diameter of the particles A and B is in the range of 100–500 μm.

3. The composite according to claim 1, characterized in that the particles A and B are rounded, preferably spherical.

4. The composite according to claim 1, characterized in that the particles A are composed of bioactive glass and that the particles B are composed of glass which does not have any bioactivity or has a weak bioactivity.

5. The composite according to claim 4, characterized in that the composition of the bioactive glass is as follows:

$SiO_2$ 53–60% by weight $Na_2O$ 0–34% by weight $K_2O$ 1–20% by weight

MgO 0–5% by weight

CaO 5–25% by weight $B_2O_3$ 0–4% by weight $P_2O_5$ 0.5–6% by weight, provided that $Na_2O+K_2O$=16–35% by weight $K_2O$+MgO=5–20% by weight MgO+CaO=10–25% by weight.

6. The composite according to claim 1, characterized in that the mixing ratio of particles A and B has been chosen so that the amount of particles A varies from about ⅕ to nearly ¼ of the total amount of the composite, preferably about ⅓ of the total amount of the composite.

7. An implant comprising a core having a recess or a through-passing hole and a bioactive structural component contained within said recess or through-passing hole and which extends to the surface of the implant, wherein said bioactive structural component comprises a layer of a porous composite which comprises:

particles A prepared from a bioactive material which will react in the physiological conditions within the body so that the outermost layer of a block manufactured from said bioactive material forms a chemical bond with surrounding host tissue, and particles B, which are prepared from a non-bioactive material or from a weakly bioactive material which under physiological conditions does not dissolve within the first few months, wherein the particles A and the particles B are partially melted together to form a porous composite having a three dimensional structure in which individual particles are connected to one at least one adjacent particle but retain a substantially spherical individual shape, characterized in that the particles A and B are essentially homogeneous in size, and wherein said particles A and particles B are approximately the same size compared to each other, and have a diameter of at least 250 microns.

8. The implant according to claim 7, characterized in that the composite layer as such is comprised of several sublayers wherein the various sublayers have a distinct mixing ratio between the particles A and B so that the content of particles A in the composite increases from the sublayer facing the implant core, towards the sublayer of the composite in contact with the tissue.

9. The implant according to claim 8, characterized in that the amount of particles A in the sublayer of the composite facing the interior of the core is 1/10 of the amount of the sublayer in question, and that the sublayer to come in contact with the tissue, is composed exclusively or almost exclusively of particles A.

10. The implant according to claim 8, characterized in that the composite within a a recess or in a through-passing hole is manufactured so that the particles A and B are introduced into the recess or the hole and subsequently sintered.

11. The implant according to claim 8, characterized in that the particles A and B required in each of the sublayers are introduced separately into the recess or the hole and subsequently sintered.

12. The implant according to claim 8, characterized in that inert particles C, preferably prepared from the material of the core, have been sintered to the surface of the recess or the through-passing hole of the implant core before the formation of or the addition of the composite into the recess or the hole.

13. The composite according to claim 1, characterized in that, in the sintering step, it has been formed into a block of the desired shape and size, which can be attached into the recess or the through-passing hole made into the implant core.

14. The composite according to claim 13, characterized in that the composite block is comprised of several sublayers wherein various sublayers have a distinct mixing ratio between the particles A and B so that the content of the particles A in the composite increases from the sublayer facing the implant core, towards the sublayer of the composite to come in contact with the tissue.

* * * * *